United States Patent [19]

Bambara et al.

[11] 4,313,583
[45] Feb. 2, 1982

[54] RAILROAD CAR WHEEL BEARING HEAT SIGNAL PROCESSING CIRCUIT

[75] Inventors: Joseph E. Bambara, North Babylon; W. Woodward Sanville, Brentwood, both of N.Y.

[73] Assignee: Servo Corporation of America, Hicksville, N.Y.

[21] Appl. No.: 135,628

[22] Filed: Mar. 31, 1980

[51] Int. Cl.³ .................. B61K 9/04; G08B 21/00
[52] U.S. Cl. .................. 246/169 A; 246/169 D; 246/DIG. 2; 308/1 A; 340/57; 340/682; 235/92 MT; 235/92 CA
[58] Field of Search .................. 340/57, 682, 584; 246/169 D, 169 A, 169 S, DIG. 1, DIG. 2; 73/355 R; 116/DIG. 38; 308/1 A; 235/92 CP, 92 MT, 92 CA

[56] References Cited

U.S. PATENT DOCUMENTS 3,100,097  8/1963  Woltersdorf ............ 246/169 D
3,731,087  5/1973  King ............ 246/169 D
4,113,211  9/1978  Glazar ............ 340/682

Primary Examiner—James J. Groody
Attorney, Agent, or Firm—Kane, Dalsimer, Kane, Sullivan and Kurucz

[57] ABSTRACT

An improved method and circuit is provided for processing waveforms from a railway car heat signal to eliminate spurious signals and to differentiate between roller bearings and friction bearings in a railroad hot box detector system. The waveforms generated by passing bearings are discretely sampled and spurious signals are eliminated by considering only those signals that fall within the crossing points of a threshold value. Discrimination between roller bearings and friction bearings is obtained by determining the ratio of the sum of the discrete values of the amplitude of the waveform within a first set of samples between the crossing points to the sum of the discrete values of the amplitude of the waveform within a second set of samples between the crossing points.

10 Claims, 4 Drawing Figures

RAILROAD CAR WHEEL BEARING HEAT SIGNAL PROCESSING CIRCUIT

BACKGROUND OF THE INVENTION

The present invention relates to railroad car hot box detectors and more particularly to a circuit for treating the heat signal generated by such detectors including discriminating between readings from roller bearings and friction bearings.

In order to protect against railroad car wheel bearing failure, most railroads utilize hot box scanners along their rights of way to view, through infrared scanners, the bearings of passing railroad cars. If an overheated bearing is detected some type of alarm is triggered to alert the engineer to stop the train and correct the potentially dangerous situation. While it is extremely important that no hot boxes be missed by the scanners, it is almost equally important that no false alarms be generated since the unscheduled stopping of a train is a costly and time consuming operation that could cause substantial disruption of schedules.

A major problem faced by the designers of hot box detectors is that railroad car wheel bearings are either of the roller bearing or friction bearing variety. While all the bearings on any particular car are usually of the same type, the different cars in a train may have different type bearings. Due to physical differences between roller and friction bearings, the output signals generated by the passing of a roller bearing are significantly higher than the signals generated by the passing of a friction bearing so that a normally operating roller bearing could appear, on an absolute scale, as an overheated friction bearing. As a result, automatic alarm systems that are based upon amplitude detection must be provided with some way of discriminating between roller bearings and friction bearings since there exists a range of amplitudes that is common to both normal roller bearings and to overheated friction bearings. A discussion of the problems associated with roller-friction bearing discrimination is contained in U.S. Pat. No. 3,812,343 which is commonly assigned with the present application.

In U.S. Pat. No. 4,113,211 which is also commonly assigned with the present application there is disclosed an analog system for discriminating between hot box detector readings taken from passing roller bearings and friction bearings. The system disclosed in this patent operates by integrating, during a time period determined by when a train wheel enters and leaves a sensing zone, the analog signal waveform and then comparing the integral to a preselected portion of the waveform to make a decision as to whether the bearing under observation is a roller bearing or friction bearing. While this system works satisfactorily in most applications, a serious problem results if a spurious signal appears while the bearing is in the sensing zone. Such signals occur quite frequently as a result of undercarriage steam pipes, sun reflections, ice reflections, etc.

In order to minimize the effect of such spurious signals in the determination of whether a passing bearing is a roller bearing or friction bearing, it is desirable to limit the active sensing zone to a time when a bearing is actually under observation. If the zone is too long, the possibility of picking up extraneous noise is increased. Conversely, if the zone is too narrow, some of the heat pulse may be lost. The problem is complicated by the fact that not all railroad car wheels are of the same diameter but generally range from between 28 to 36 inches. As a result, the bearing heat signal could and generally does occupy only a fraction of the sensing zone.

In view of the above, it is a principal object of the present invention to provide an improved hot box signal processing circuit in which virtually all spurious signals which are generated when the wheel is within the sensing zone are eliminated. A further object is to provide such a circuit which is compatible with existing equipment and which may readily and economically be retrofitted into such equipment.

Still further objects will be obvious from the foregoing description of the invention.

SUMMARY OF THE INVENTION

The above and other beneficial objects and advantages are attained in accordance with the present invention by providing an improved circuit which includes means for discretely sampling the output of an infrared detector at fixed space intervals while a train wheel is within the detector sensing zone. The detected voltage level for each sample is summed and then divided by the number of significant samples (i.e., number of samples with readings above zero). The resultant preliminary heat value is then divided by a fixed constant to establish a threshold value. The crossing points of the heat signal over the threshold are then determined and the voltage levels above the threshold generated between the crossing points are added and divided by the number of samples between the crossing points. This last resultant value may serve as an absolute alarm trigger and also stored for further processing. The sum of voltage levels reached during a portion of the number of samples between the crossing points is fed to a comparator. The other inputs to the comparator comprise the sum of the voltage levels reached during another portion. The output of the comparator is indicative of whether the bearing under observation is a roller or a friction bearing.

DETAILED DESCRIPTION OF THE PREFERRED EMBODIMENT

Figure 1:
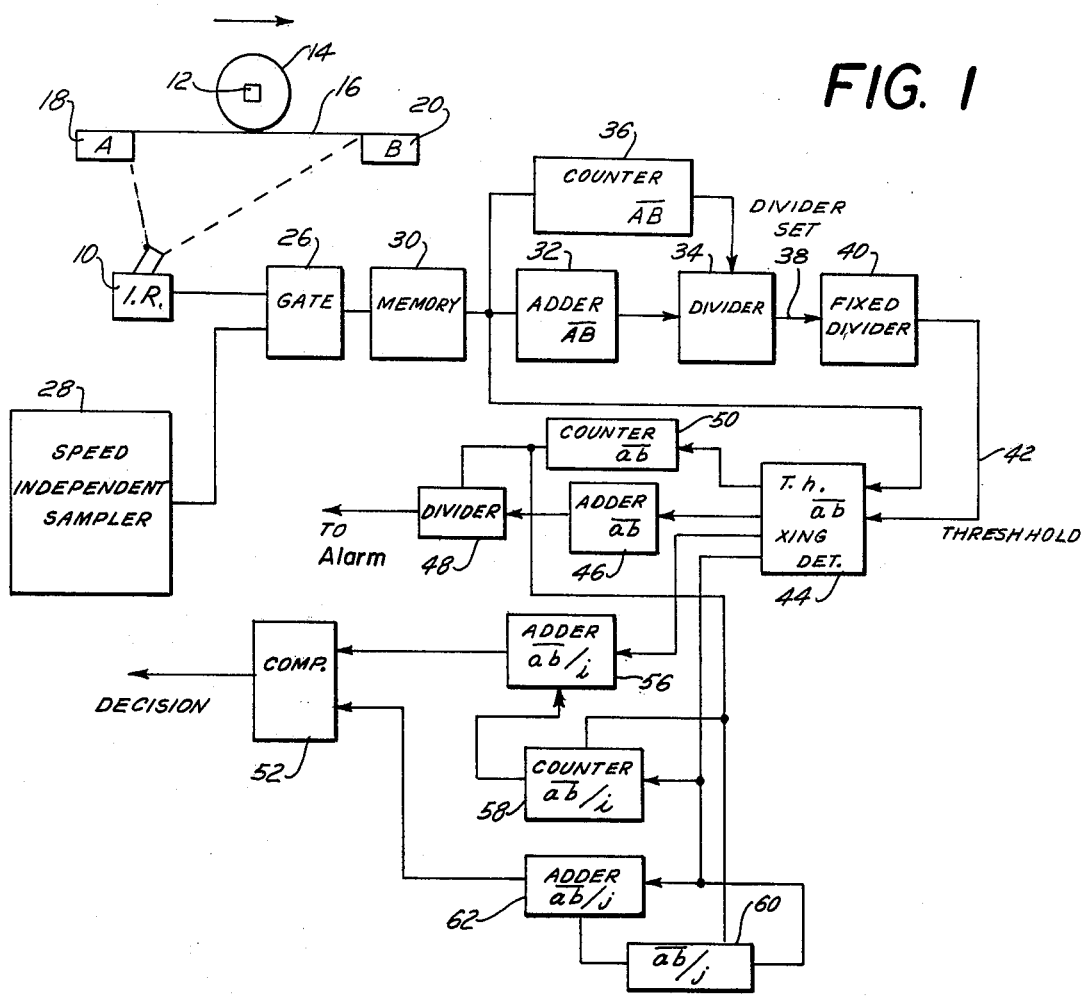
FIG. 1 is a simplified block diagram of the heat signal processing circuit of the present invention.

Reference is now made to the drawings and to FIG. 1 in particular wherein a heat signal processing circuit in accordance with the present invention is shown connected with a conventional infrared hot box detector 10 such as the SERVOSAFE HOT BOX DETECTIVE marketed by the Servo Corporation of America, Hicksville, N.Y.

The details of the infrared scanner 10 are generally well known to those familiar with the art. It suffices to say for the present application that radiation from a passing wheel bearing is imaged through suitable optics permitting the scanner to "view" the bearing 12 of a passing wheel 14 as the wheel passes along a length of track 16 defined by wheel sensors 18 and 20 designated respectively "A" and "B". Ideally, for a passing roller bearing, the output signal of scanner 10 would be a waveform generally shaped as in FIG. 3A. For a passing friction bearing, the ideal waveform would be of the shape depicted in FIG. 3B. Due to noise and other signal transmission perturbations the actual output signal of detector 10 will be considerably distorted from the idealized waveforms of FIGS. 3A and 3B. However, it has been observed that even in a highly distorted form, the waveform for a friction bearing declines far more rapidly than it rises while the waveform for a roller bearing generally rises and falls at equal rates. Use is made of this observed phenomena.

In accordance with the present invention, the output of scanner 10 comprises a signal, the duration of which is generally co-extensive with the time it takes for the wheel to go from wheel trip A to wheel trip B and consisting of a bearing heat signal 22 which may be accompanied by spurious heat signals 24 such as from a steam pipe, wheel flash, etc. The spurious signal 24 is eliminated and the nature of the bearing is determined utilizing the circuit of FIG. 1 in the following manner.

Referring to FIG. 1, the output of scanner 10 is fed to gate 26 along with the output of a speed independent sampling circuit 28. The circuit 28 is described in detail in the commonly assigned co-pending application Ser. No. 125,487 filed Feb. 28, 1980 for SPEED INDEPENDENT SYSTEM FOR OBTAINING PRESELECTED NUMBERS OF SAMPLES FROM OBJECT MOVING ALONG A FIXED PATH. In essence, circuit 28 serves to divide the distance $\overline{AB}$ into N number of equispaced intervals in time regardless of how long it takes the wheel to trip wheel sensors 18 and 20. The output of the gate 26 which comprises a series of discrete voltages corresponding to points along waveform 22 is fed to a suitable storage device 30 for subsequent recall as required by the processing equipment to be described forthwith.

Figure 2:
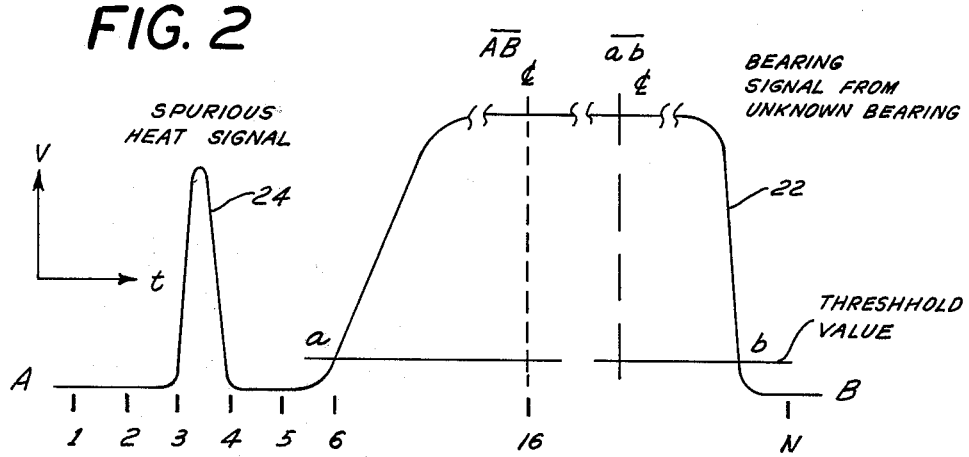
FIG. 2 is a waveform diagram depicting a bearing signal from an unknown bearing source along with a spurious signal; and, FIGS. 3A and B represent respectively idealized roller bearing and friction bearing waveforms.

The various voltage levels from gate 26 are added in adder 32. The output of adder 32 is divided by divider 34 the value of which is set by counter 36 which determines the actual number of significant samples (i.e., samples at which a voltage level other than zero (or a preselected base level)) is detected. The output of divider 34 corresponds to a preliminary heat value 38 which, it should be noted, includes a voltage level corresponding to the heat value generated by the spurious heat signal 24. The preliminary heat value 38 is then further divided by a fixed divider 40. The output 42 of divider 40 establishes a threshold value indicated by the line $\overline{a\,b}$ on FIG. 2. It has been found that for sampler 28 taking 32 samples in the time required for a wheel to pass 27 inches from A to B, divider 40 should divide by 8 to establish a proper working threshold for the output from a conventional IR scanner 10.

The output of memory 30 is also fed along with the output 42 of divider 40 to a threshold crossing determinating circuit 44 to determine the points in time (a and b) wherein the waveform 22 crosses the threshold determined by the output 42 of divider 40. This may conveniently be done by first determining a point near the center of $\overline{AB}$ and then looking backward and forward to determine when the threshold is crossed. This may readily be done since circuit 28 divides the time interval to cross $\overline{AB}$ into a known number of equispaced samples. Once the threshold crossing points a and b are determined, the voltage levels of waveform 22 during the sampling period occurring between the threshold crossings are then added in adder 46 and the sum is divided by divider 48. The value of divider 48 is determined by counter 50 which determines the number of samples to have occurred between the crossing points a and b.

The output of divider 48 represents an absolute heat value which, if exceeding a preset limit may be used to trigger an alarm. The output of counter 50 also serves to determine two portions of $\overline{a\,b}$ through counters 58 and 60. Counter 58 enables adder 56 to add the sum of voltage levels reached during a first portion of $\overline{a\,b}$. Counter 60 enables adder 62 to add the sum of voltage levels reached during a second portion of $\overline{a\,b}$. The outputs of the adders 56 and 62 are fed to comparator 52.

Since the voltage samples are taken at equispaced points (in time), the sums, of the voltage levels (i.e., outputs of adders 56 and 62) are each roughly equal of the integrals of the portions of the waveform and thus are representative of the areas under the waveform for each portion. In a successful practice of the invention, the portions selected were respectively the first and second halves of $\overline{a\,b}$.

Figure 3A:
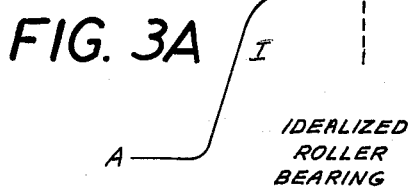
Figure 3B:
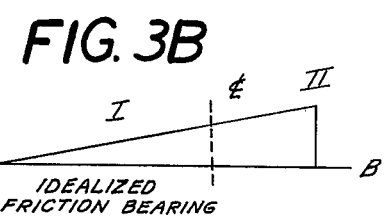

As previously mentioned for a roller bearing, the areas generally designated by Roman numerals I and II in FIG. 3A on opposite sides of the $\overline{a\,b}$ center line are substantially equal whereas for a friction bearing the area designated by Roman numeral I of FIG. 3B on one side of the $\overline{a\,b}$ center line is approximately ½ the area designated by Roman numeral II on the other side of the center line. Accordingly, if the output of adder 56 is less than ⅔ the output of adder 62 the bearing is treated as a friction bearing.

It is to be noted that in the above determination, once the points a and b are determined, the voltage levels generated by virtue of the spurious heat signal 24 are eliminated from further consideration and play no part in either the determination of the nature of the bearing under consideration or the heat levels attained. It should be noted that the number of voltage samples between a and b is a measure of the size of the bearing, and the location of the voltage samples between a and b relative to the samples in A to B is a measure of the wheel size. Accordingly, the objectives of the present invention are effectively attained.

Having thus described the invention, what is claimed is:

1. In a railroad hot box detector system of the type including infrared responsive scanner means associated with a sensing zone along a section of track adapted to scan bearings of a railroad car within said sensing zone and to generate an output voltage signal in response thereto having an amplitude and waveform indicative of the type of bearing being scanned and a sampling circuit adapted to sample the output of said scanner means into a preselected number of discrete samples the improvement comprising:

means for establishing a threshold signal level related to the average of the discrete voltage levels;

means for determining the number of discrete samples falling between the crossing points of said waveform through said threshold; and means for averaging the discrete voltage levels of the samples falling between the crossing points whereby to obtain a signal indicative of the heat condition of the bearing being scanned.

2. The invention in accordance with claim 1 further comprising:

means for obtaining a first predetermined portion of the samples falling between the crossing points;

means for obtaining the sum of the voltage levels during said first predetermined portion;

means for obtaining a second predetermined portion of the samples falling between the crossing points;

means for obtaining the sum of the voltage levels during said second predetermined portion; and means for comparing said first and second sums to obtain information indicative of the type of bearing being scanned.

3. In a railroad hot box detector system of the type including infrared responsive scanner means associated with a sensing zone along a section of track adapted to scan bearings of a railroad car within said sensing zone and to generate an output voltage signal in response thereto having an amplitude and waveform indicative of the type of bearing being scanned and a sampling circuit adapted to sample the output of said scanner means into a preselected number of discrete samples the improvement comprising:

means for establishing a threshold signal level related to the average of the discrete voltage levels;

means for determining the number of discrete samples falling between the crossing points of said waveform through said threshold;

means for obtaining a first predetermined portion of the samples falling between the crossing points;

means for obtaining the sum of the voltage levels during said first predetermined portion;

means for obtaining a second predetermined portion of the samples falling between the crossing points;

means for obtaining the sum of the voltage levels during said second preselected portion, and, means for comparing said first and second sums to obtain information indicative of the type of bearing being scanned.

4. The invention in accordance with claim 1 or 3 wherein said threshold establishing means includes means for adding the sum of said discrete voltage levels and a variable divider for dividing said sum, the divisor of said variable divider comprising the number of discrete voltage levels added.

5. The invention in accordance with claims 1 or 3 wherein said threshold establishing means includes means for adding the sum of said discrete voltage levels; a first divider for dividing said sum, the divisor of said first divider comprising the number of discrete voltage levels added; and a second divider connected to the output of said first divider, the divisor of said second divider comprising a fixed value and the output of said second divider comprising said threshold.

6. The method for eliminating spurious signals in the processing of a railroad car bearing heat signal waveform comprising the steps of:

(a) scanning the bearings of a railroad car within a sensing zone along a length of track to generate a waveform indicative of the heat condition of the bearing being scanned;

(b) sampling the output of said scanner into a preselected number of discrete samples;

(c) adding the voltage levels of all the samples of said waveform in excess of zero and dividing the sum so obtained by the number of samples added to obtain a threshold; and (d) determining the points where the waveform would cross said threshold and eliminating all the sample points outside said crossing whereby to eliminate spurious signals.

7. The method in accordance with claim 6 comprising the further steps of:

determining the sum of the voltage levels of the samples of said waveform within a first portion of the threshold crossing points;

determining the sum of the voltage levels of a second portion of the samples of said waveform between the threshold crossing points; and, obtaining the ratio of the sum of the first portion voltage levels to the sum of the voltage levels of the second portion whereby to obtain a number indicative of the type of bearing under investigation.

8. The method for discriminating between waveforms generated by roller bearings and friction bearings in the processing of a railway car bearing heat signal waveform comprising the steps of:

(a) scanning the bearings of a railroad car within a sensing zone along a length of track to generate a waveform indicative of the type of bearing being scanned;

(b) sampling the output of said scanner into a preselected number of discrete samples;

(c) adding the voltage levels of all the samples of said waveform in excess of zero and dividing the sum so obtained by the number of samples added to obtain a threshold;

(d) determining the points where the waveform would cross said threshold and eliminating all the sample points outside said crossing;

(e) determining the sum of the voltage levels of the samples of said waveform within a first portion of the threshold crossing points;

(f) determining the sum of the voltage levels of a second portion of the samples of said waveform between the threshold crossing points; and, (g) obtaining the ratio of the sum of the first portion voltage levels to the sum of the voltage levels of the second portion whereby to obtain a number indicative of the type of bearing under investigation.

9. The method in accordance with claims 6 or 8 further comprising the step of determining the ratio of the threshold portion of the waveform between the crossing points to said sensing zone whereby to obtain an indication of the size of the bearing under consideration.

10. The method in accordance with claims 6 or 8 further comprising the step of determining the relative position of the threshold portion of the waveform between the crossing points to said sensing zone whereby to obtain an indication of the size of the wheel under consideration.

* * * * *